(12) United States Patent
Fukuda et al.

(10) Patent No.: US 11,701,011 B2
(45) Date of Patent: Jul. 18, 2023

(54) BIOLOGICAL INFORMATION DETECTION DEVICE AND BIOLOGICAL INFORMATION DETECTION METHOD

(71) Applicant: HITACHI, LTD., Tokyo (JP)

(72) Inventors: Nobuhiro Fukuda, Tokyo (JP); Yuichi Nonaka, Tokyo (JP); Yuto Komatsu, Tokyo (JP); Charles Limasanches, Tokyo (JP); Takashi Numata, Tokyo (JP); Hironori Wakana, Tokyo (JP); Masashi Kiguchi, Tokyo (JP)

(73) Assignee: HITACHI, LTD., Tokyo (JP)

(*) Notice: Subject to any disclaimer, the term of this patent is extended or adjusted under 35 U.S.C. 154(b) by 294 days.

(21) Appl. No.: 17/004,371

(22) Filed: Aug. 27, 2020

(65) Prior Publication Data

US 2021/0085196 A1 Mar. 25, 2021

(30) Foreign Application Priority Data

Sep. 19, 2019 (JP) .................................. 2019-170215

(51) Int. Cl.
*A61B 5/021* (2006.01)
*A61B 5/103* (2006.01)
(Continued)

(52) U.S. Cl.
CPC ........ *A61B 5/02125* (2013.01); *A61B 5/0077* (2013.01); *A61B 5/1032* (2013.01); *A61B 5/1176* (2013.01)

(58) Field of Classification Search
CPC . A61B 5/02125; A61B 5/0077; A61B 5/1032; A61B 5/1176
See application file for complete search history.

(56) References Cited

U.S. PATENT DOCUMENTS

2016/0228011 A1\* 8/2016 Tsubaki ................. A61B 5/024
2017/0007137 A1 1/2017 Hong et al.
(Continued)

FOREIGN PATENT DOCUMENTS

JP 2012-239661 A 12/2012
JP 2016-190022 A 11/2016
(Continued)

OTHER PUBLICATIONS

U.S. Appl. No. 15/941,471, filed Mar. 2018, Fukuda; Nobuhiro.\*
(Continued)

*Primary Examiner* — Eric F Winakur
*Assistant Examiner* — Jonathan Drew Moroneso
(74) *Attorney, Agent, or Firm* — Volpe Koenig

(57) ABSTRACT

Provided is a biological information detection device including: an image acquisition unit that acquires an image composed of image signals including a plurality of wavelength components obtained by capturing reflected light from an object; a region division unit that divides the image into a plurality of regions for each frame; a local pulse wave detection unit that detects a pulse wave based on wavelength fluctuation between frames for each of the regions; and a blood pressure estimation unit that calculates propagation velocity of the pulse wave based on an appearance time difference of patterns of the pulse waves in two or more regions extracted based on an appearance order of the patterns of the pulse waves in the plurality of regions, and estimates a blood pressure based on the propagation velocity of the pulse wave.

11 Claims, 11 Drawing Sheets

(51) Int. Cl.
*A61B 5/00* (2006.01)
*A61B 5/1171* (2016.01)

(56) References Cited

U.S. PATENT DOCUMENTS

| | | | |
|---|---|---|---|
| 2018/0042486 A1 | 2/2018 | Yoshizawa et al. | |
| 2018/0150682 A1* | 5/2018 | Fukuda | G06V 10/56 |
| 2019/0125197 A1 | 5/2019 | Fukuda et al. | |
| 2021/0219852 A1* | 7/2021 | Colburn | A61B 5/02108 |
| 2022/0104715 A1* | 4/2022 | Ogawa | A61B 5/02108 |

FOREIGN PATENT DOCUMENTS

| | | |
|---|---|---|
| JP | 2018-86130 A | 6/2018 |
| JP | 2019-80811 A | 5/2019 |

OTHER PUBLICATIONS

U.S. Appl. No. 16/818,189, filed Mar. 2020, Fukuda; Nobuhiro.*
Moens, a. Isebree and Korteweg, D.J., "on the speed of propagation of waves in elastic tubes" A S Tijsseling, Department of Mathematics and Computer Science, Eindhoven University of Technology, The Netherlands A Anders, School of Mechanical and Systems Engineering, University of Newcastle upon Tyne, United Kingdom Oct. 2012.
Japanese Office Action dated Dec. 6, 2022 for Japanese Patent Application No. 2019-170215.
Japanese Office Action dated May 30, 2023 for Japanese Patent Application No. 2019-170215.

* cited by examiner

BIOLOGICAL INFORMATION DETECTION DEVICE AND BIOLOGICAL INFORMATION DETECTION METHOD

CLAIM OF PRIORITY

The present application claims priority from Japanese patent application JP 2019-170215 filed on Sep. 19, 2019, the content of which is hereby incorporated by reference into this application.

BACKGROUND OF THE INVENTION

1. Field of the Invention

The present invention relates to a device that detects biological information.

2. Description of the Related Art

As a technique for acquiring biological information, there is a technique capable of performing detection in real time in a non-contact manner using a microwave or a camera. In particular, in recent years, pulse detection using a camera has become popular along with progress in miniaturization of a camera module, which has been mounted on a portable terminal including a smartphone.

As a technique for detecting a pulse by imaging, there is a method of specifying a pulse signal from a spectral distribution of a time-series signal (JP 2012-239661 A). Further, there is a method of specifying a pulse signal from fluctuation in a wavelength distribution of light entering a camera, that is, fluctuation in the center of gravity of a color distribution (JP 2019-080811 A).

In performing blood pressure measurement in real-time, an invasive method in which a blood pressure is directly monitored using a catheter is often adopted in a medical practice. However, in recent years, there is known a non-invasive method in which a sensor is pressed against an artery and the fluctuation of the internal pressure of the artery that beats against this sensor is converted into an electric signal for measurement. It is also known to estimate a blood pressure by the Moens-Korteweg equation showing the relationship between the pulse wave propagation velocity and the incremental elastic modulus of the artery wall (Tijsseling A S, Anderson A. (2012) "A. Isebree Moens and DJ Korteweg: on the speed of propagation of waves in elastic tubes", BHR Group, Proc. Of the 11th Int. Conf. On Pressure Surges (Editor Sandy Anderson), Lisbon, Portugal, October (2012)). There is a method of applying this equation to estimate a blood pressure from a camera image (JP 2018-086130 A).

SUMMARY OF THE INVENTION

Under such circumstances, various studies for monitoring biological information are being conducted to detect sudden changes in the condition of elderly people or during driving of a car, for example, and in blood pressure measurement, a non-contact measurement method, which gives a small load to a subject, is important. Therefore, non-contact blood pressure measurement can be performed by performing pulse detection using a camera and obtaining the pulse wave propagation velocity based on the interval between two different points along an artery and the phase difference between pulse waves. The pulse detection by the camera is generally performed on the face as an imaging target, but may be performed on exposed skin near an artery.

Since the image of the face or another exposed skin is, for example, reflected light when illumination light is applied to the face, in a conventional method using a RGB signal, a change in the spectral intensity of reflected light of three colors is observed. Therefore, when steady light impinges on the face, the pulse can be detected stably, but when an external light change in the imaging environment occurs, each spectrum is affected and erroneous detection occurs. Although noise can be separated by applying the independent component analysis, it is difficult to specify a physical quantity after conversion.

It is not possible to accurately detect a pulse wave image in all regions of the face or the exposed skin. For example, even when such an optical disturbance is excluded, and, for example, a pulse wave is detected in a region along an artery, it may be difficult to detect the pulse wave propagation velocity due to individual differences in blood vessel positions, physiological disturbances such as backflow of blood, and mixing of pulse waves by veins and arteries in the same detection region.

In order to solve at least one of the problems described above, according to the present invention, there is provided a biological information detection device including: an image acquisition unit that acquires an image composed of image signals including a plurality of wavelength components obtained by capturing reflected light from an object; a region division unit that divides the image into a plurality of regions for each frame; a local pulse wave detection unit that detects a pulse wave based on wavelength fluctuation between frames for each of the regions; and a blood pressure estimation unit that calculates propagation velocity of the pulse wave based on an appearance time difference of patterns of the pulse waves in two or more regions extracted based on an appearance order of the patterns of the pulse waves in the plurality of regions, and estimates a blood pressure based on the propagation velocity of the pulse wave.

According to one embodiment of the present invention, an optical disturbance and a physiological disturbance can be eliminated, and a non-contact blood pressure detection method can be provided by accurately calculating a pulse wave propagation velocity. Problems, configurations, and effects other than those described above will be clarified by the following description of embodiments.

DESCRIPTION OF THE PREFERRED EMBODIMENTS

Figure 1:
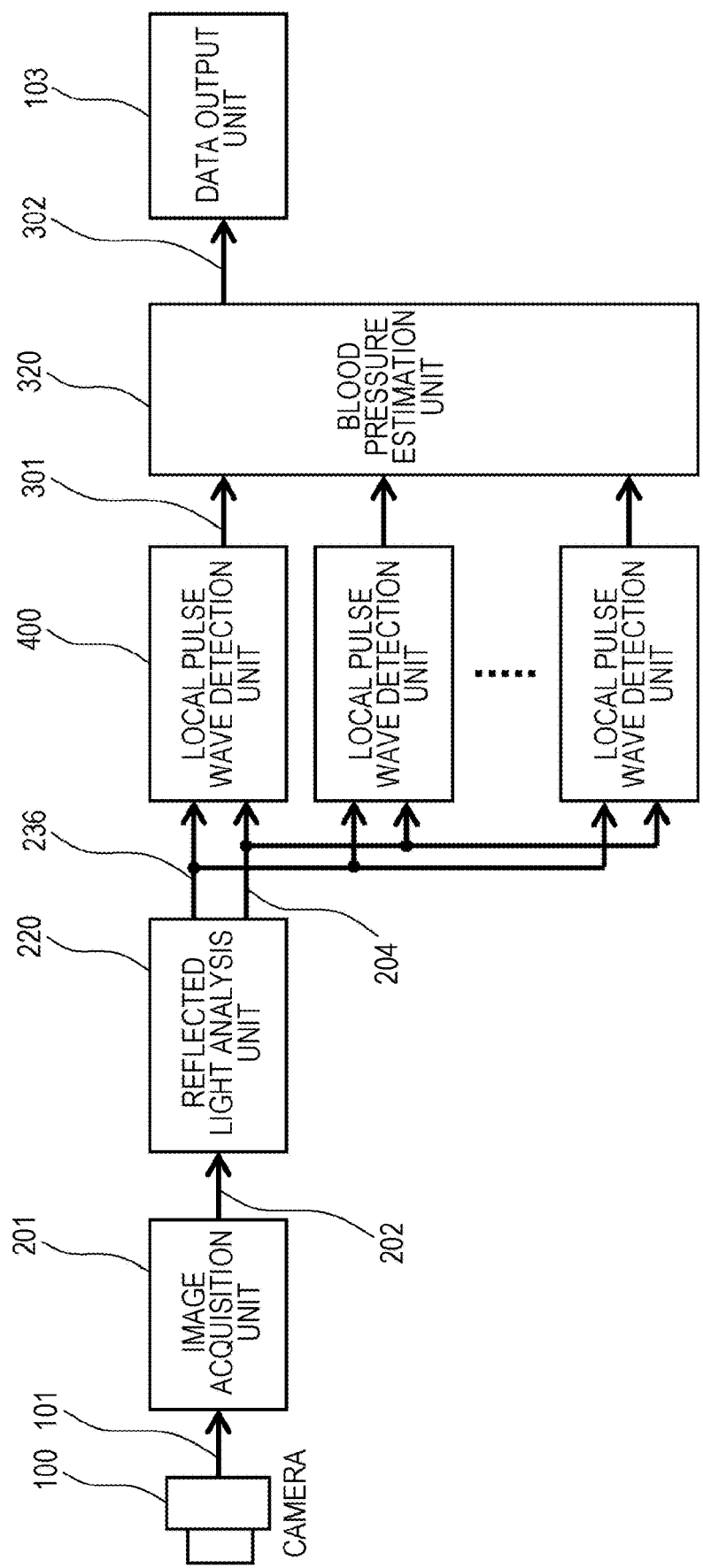
FIG. 1 is a block diagram illustrating an example of a configuration of a biological information detection device according to a first embodiment of the present invention.

Hereinafter, embodiments of the present invention will be described with reference to the drawings, but the present invention is not necessarily limited to these embodiments. In the drawings describing the embodiments, the same members are denoted by the same reference numerals, and a repeated description thereof will be omitted.

First Embodiment

In the present embodiment, description is made of an example of a biological information detection device that excludes optical disturbance by detecting a pulse wave based on wavelength fluctuation of reflected light for each divided region from a captured face image, calculates a phase difference from a pulse wave pattern of each region, and estimates a blood pressure.

FIG. 1 is a block diagram illustrating an example of a configuration of a biological information detection device according to a first embodiment of the present invention.

The biological information detection device according to the present embodiment includes a camera 100 configured by an image signal including a plurality of wavelength components, an image acquisition unit 201, a reflected light analysis unit 220, a plurality of local pulse wave detection units 400, a blood pressure estimation unit 320, and a data output unit 103.

The image acquisition unit 201 receives an imaging data signal 101 acquired from the camera 100 as an input, and outputs an image RGB signal 202. The reflected light analysis unit 220 receives the RGB signal 202 as an input signal and outputs a level signal 236 and a wavelength data signal 204. In the present configuration, the configuration in which the biological information detection device includes the camera 100 has been described. However, instead of the camera 100, data in which a camera image is stored in advance and an image playback device may be used.

Figure 2:
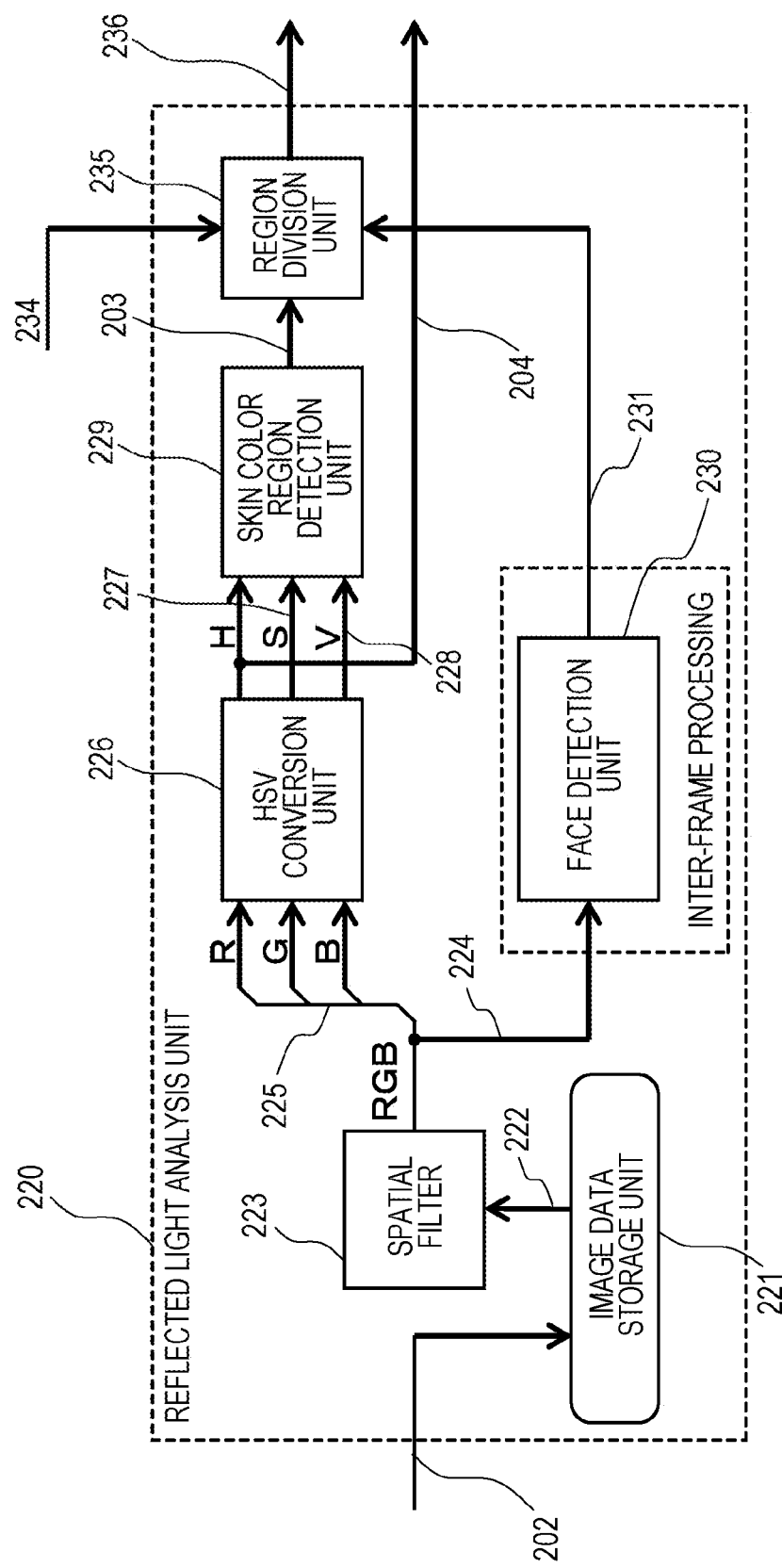
FIG. 2 is a block diagram illustrating an example of a reflected light analysis unit of the biological information detection device according to the first embodiment of the present invention.

FIG. 2 is a block diagram illustrating an example of the reflected light analysis unit 220 of the biological information detection device according to the first embodiment of the present invention.

The reflected light analysis unit 220 includes an image data storage unit 221, a spatial filter 223, an HSV conversion unit 226, and a skin color region detection unit 229, and performs image processing for each pixel. The image data storage unit 221 receives the RGB signal 202 as an input and outputs a delayed RGB signal 222 having a line delay corresponding to a tap of a convolution kernel. The spatial filter 223 receives the delayed RGB signal 222 as an input, and weights and averages, for example, a pixel of interest and its surrounding pixels and outputs a smoothed RGB signal 224. The HSV conversion unit 226 receives an unpacked signal 225 obtained by decomposing the smoothed RGB signal 224 into R (red), G (green), and B (blue) signals as an input, and converts them into an H signal (hue), that is, the wavelength data signal 204, a S signal (saturation) 227, and a V signal (color value) 228.

The reflected light analysis unit 220 further includes a face detection unit 230 that performs inter-frame processing. The face detection unit 230 receives the smoothed RGB signal 224 as an input, performs face detection by, for example, the Viola-Jones method, and outputs a face region signal 231. The skin color region detection unit 229 receives the H signal (hue) 204, the S signal (saturation) 227, and the V signal (color value) as inputs, and outputs the level signal 236 indicating a skin color region illustrated in FIG. 13.

Figure 9:
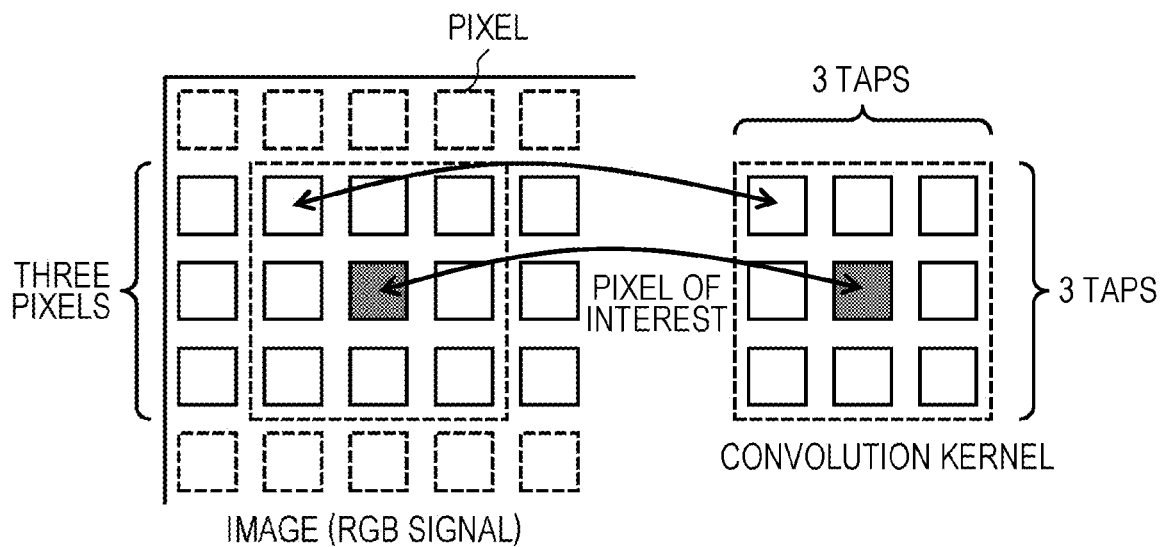
FIG. 9 is a diagram illustrating an example of a spatial filter according to the first embodiment of the present invention.

FIG. 9 is a diagram illustrating an example of the spatial filter according to the first embodiment of the present invention.

FIG. 9 is an example in which a convolution kernel of 3 taps in the vertical and horizontal directions, that is, a 3×3 convolution kernel is applied to an image, and a value obtained by performing a convolution operation with the kernel around a pixel of interest in the image serves as the smoothed RGB signal 224. The value of the kernel is a coefficient of the weighted average, and the total value thereof is 1.0. For example, an average distribution or a Gaussian distribution can be used for smoothing.

Figure 10:
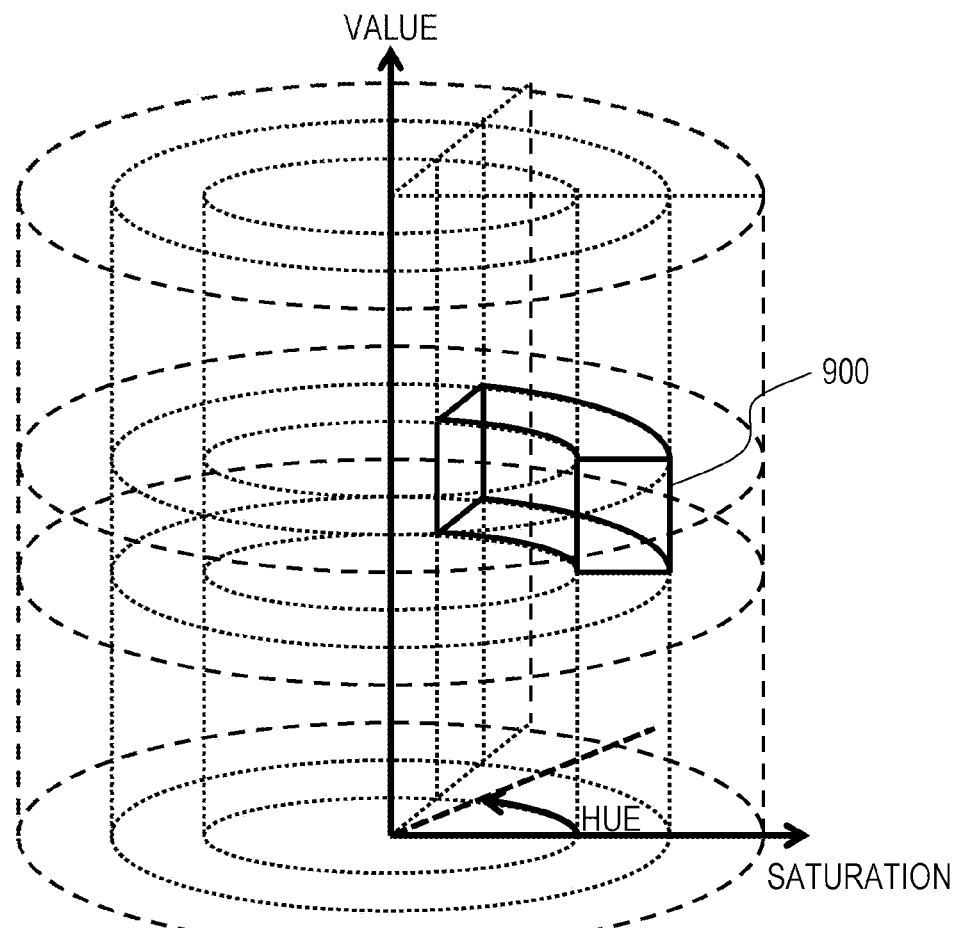
FIG. 10 is a diagram illustrating an example of a designated range of an HSV color space and a partial color space according to the first embodiment of the present invention.

FIG. 10 is a diagram illustrating an example of a designated range of an HSV color space and a partial color space according to the first embodiment of the present invention.

FIG. 10 illustrates the HSV color space in cylindrical coordinates. The vertical axis represents the brightness of color by Value, that is, color value, and the axis in the radial direction represents the density of color by Saturation. The rotation angle is Hue. The hue is independent of the intensity and the density, and is considered to correspond to a wavelength component of the reflected light, assuming that imaging captures reflection of light. Similarly, the color value can be considered to indicate the intensity at a particular wavelength. The skin color region detection unit 229 designates a skin color region using a partial color space like a region 900 in FIG. 10 in this HSV color space, and when the HSV value is included in the skin color region, the skin color region detection unit 229 may output 1 as a level signal 203, and when the HSV value is not included, may output 0.

Figure 11:
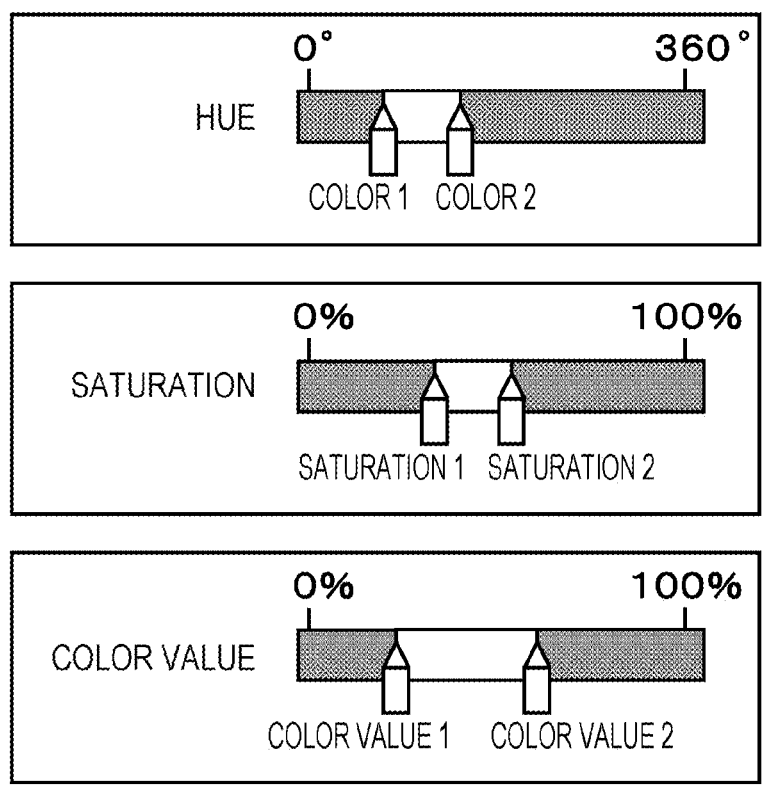
FIG. 11 is a diagram illustrating an example of a setting method for a partial color space according to the first embodiment of the present invention.

FIG. 11 is a diagram illustrating an example of a setting method for a partial color space according to the first embodiment of the present invention.

For example, as illustrated in FIG. 11, the data output unit 103 of the biological information detection device may display bars indicating the entire ranges of the hue, the saturation, and the color value, and icons each indicating both ends of the range designated on the bar (for example, "color 1" and "color 2" designating the color), and the range may be designated by operating the icon.

For example, for the hue, the bar in the range from 0 to 360 degrees is displayed. 0 degrees=360 degrees is red, 120 degrees is green, and 240 degrees is blue. The section designated by the color 1 and the color 2 as illustrated in FIG. 11 (that is, the range of the hue from the color 1 to color 2) may be set as the corresponding range. Similarly, for the saturation, 0% is light color, and 100% is dark color. For the color value, 0% is dark color, and 100% is bright color. The range may be designated by designating both ends of the range (for example, the saturation 1 and the saturation 2 for the saturation, the color value 1 and the color value 2 for the color value). For example, depending on the type of illumination used when the camera 100 photographs a person and individual differences in skin color of each person to be photographed, the color and the brightness of a skin to be photographed may be significantly different. However, by setting appropriate ranges of the hue, the saturation, and the color value using the setting method as described above, the pulse can be appropriately detected in accordance with the photographing environment and the nature of a person to be photographed (for example, skin color).

The reflected light analysis unit 220 in FIG. 2 further includes a region division unit 235. The region division unit 235 receives the face region signal 231 output from the face detection unit 230, the level signal 203 output from the skin color region detection unit 229, and a division number parameter 234 of the face region as inputs. The region division unit 235 divides the face region into a plurality of regions, and passes the level signal 236 to the local pulse wave detection unit 400 corresponding to each region.

Figure 4:
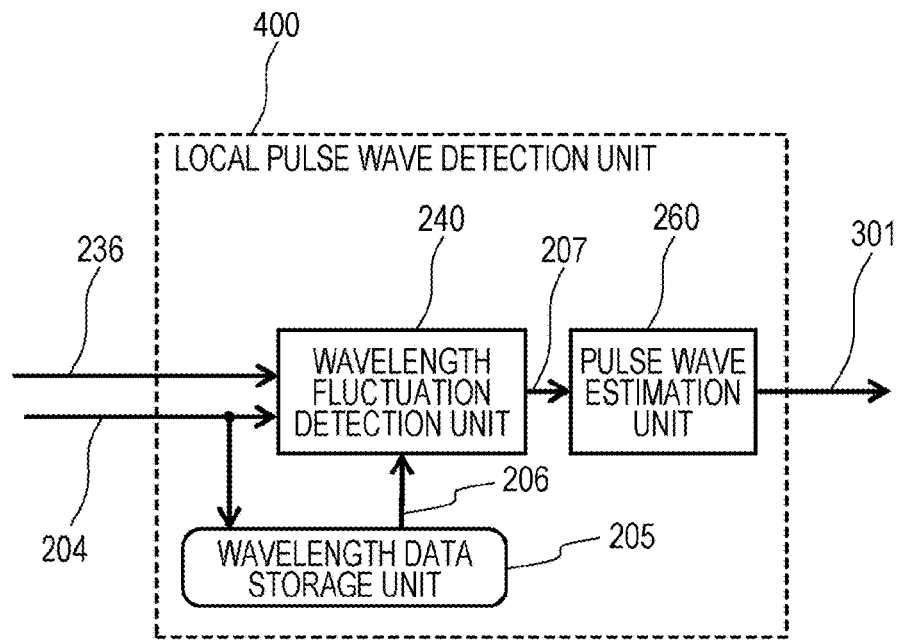
FIG. 4 is a block diagram illustrating an example of a local pulse wave detection unit of the biological information detection device according to the first embodiment of the present invention.

FIG. 4 is a block diagram illustrating an example of the local pulse wave detection unit 400 of the biological information detection device according to the first embodiment of the present invention.

The local pulse wave detection unit 400 includes a wavelength data storage unit 205, a wavelength fluctuation detection unit 240, and a pulse wave estimation unit 260. Details of these will be described later (see FIGS. 5 to 7).

Figure 12:
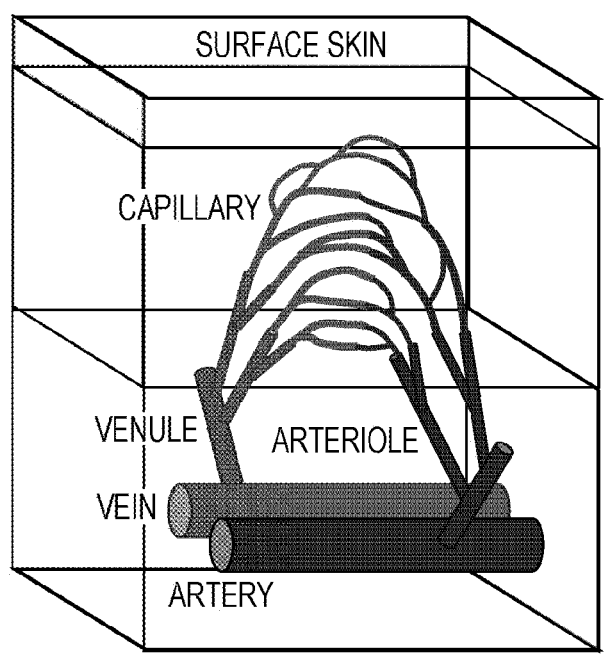
FIG. 12 is a diagram illustrating a flow of a blood flow relating to a detection target by the biological information detection device according to the first embodiment of the present invention.

FIG. 12 is a diagram illustrating a flow of a blood flow relating to a detection target by the biological information detection device according to the first embodiment of the present invention.

Blood pumped from a heart flows from arteries through arterioles into capillaries, supplies oxygen and nutrients, flows through venules into veins, and sends the blood back to the heart. The biological information detection device of the present embodiment observes such a blood flow by observing absorption and scattering of light into the skin through the camera 100. However, for example, there are individual differences in the arrangement of blood vessels, and the direction of a blood flow to a face is not limited to one direction, so that pulse wave measurement in a local region is under the influence of various disturbances.

Figure 13:
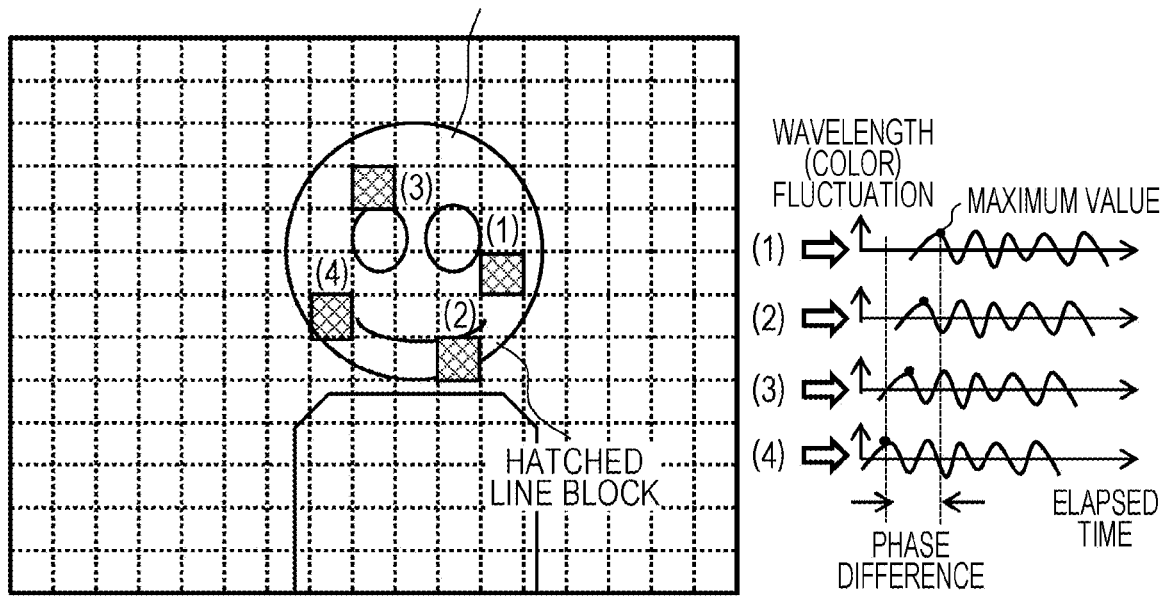
FIG. 13 is a diagram illustrating an example of region division and pulse wave propagation velocity detection in the first embodiment of the present invention.

FIG. 13 is a diagram illustrating an example of region division and pulse wave propagation velocity detection according to the first embodiment of the present invention.

A camera image is subdivided into dotted line regions as illustrated in FIG. 13, and after the skin color is detected by the skin color region detection unit 229, the region which is a calculation target of the pulse signal is determined. The shaded regions denoted by (1) to (4) in the figure are the skin color regions which are calculation targets. Although the blood flow flows along the arteries, the direction of the blood flow to the extremities does not necessarily match the direction of the blood flow through the arteries. Therefore, as in (1) to (4) in the figure, the order in which the pulse wave appears does not always match the flow of the facial artery, and there is considered a case where the blood flows discontinuously (for example, in a manner that the pulse wave appears in the order of (4), (3), (2), and (1)). Therefore, instead of following the blood flow of the artery, in the blood pressure estimation unit 320, according to the order in which a pulse wave pattern of a pulse wave signal 301 for each local region (for example, the maximum value or the minimum value of the pulse wave) appears, the pulse wave propagation velocity may be calculated based on the difference between the first one and last one of the order, that is, the phase difference (in other words, the appearance time difference) between (1) and (4) in the figure.

Figure 14:
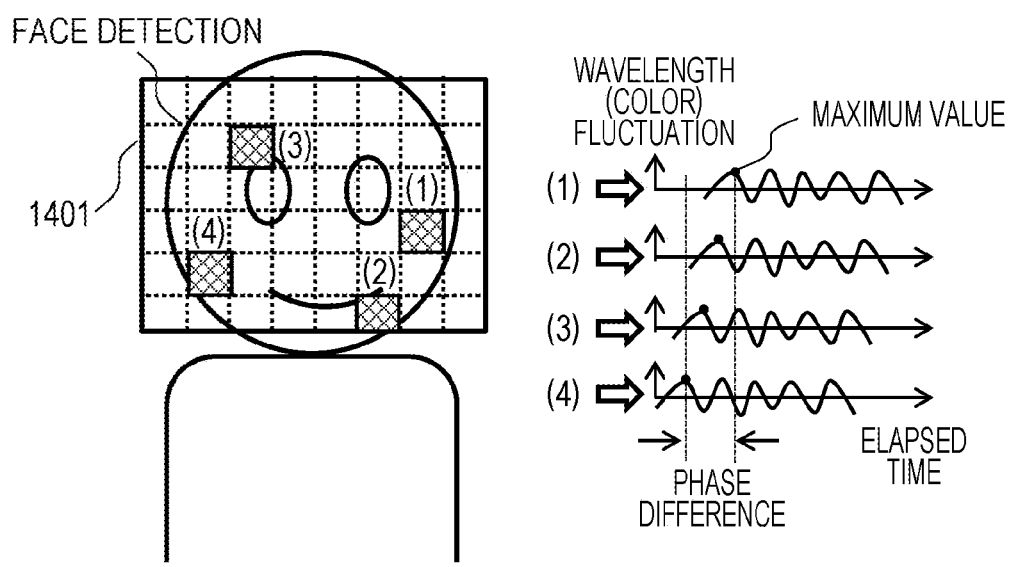
FIG. 14 is a diagram illustrating an example of region division and pulse wave propagation velocity detection after face detection in the first embodiment of the present invention.

FIG. 14 is a diagram illustrating an example of region division and pulse wave propagation velocity detection after face detection according to the first embodiment of the present invention.

Eyes, mouth, nose, eyebrows, ears, and the like can be given as characteristic portions constituting the face. In this embodiment, the description will be made using the eyes and mouth. For example, face features such as eyes and mouths are identified as face features which are detected as in FIG. 14 using a feature classifier such as Haar-like or LBP (Local Binary Pattern) and can be calculated as, for example, a rectangular region 1401. Therefore, as illustrated in FIG. 14, the rectangular region 1401 surrounded by the solid line is divided into a plurality of dotted line regions, and a pulse wave pattern is detected in each of the regions. According to the order in which the pulse wave pattern appears, the pulse wave propagation velocity may be calculated based on the difference between the first one and last one of the order, that is, the phase difference (in other words, the appearance time difference) between (1) and (4) in the figure.

According to the method in FIG. 13, the detection processing of the face region can be omitted, but the processing for detecting the pulse wave is also performed on the region other than the face (in other words, other than the skin of the person). On the other hand, according to the method in FIG. 14, it is necessary to perform the detection processing for the face region, but pulse wave detection for regions other than the face is omitted. An appropriate method can be selected depending on the mode of actual use of the biological information detection device (for example, where the device is installed and used in what situation).

Here, FIGS. 13 and 14 show an example of using the appearance time difference between the first one and the last one of the order of appearance of the pulse wave pattern, but this is an example, and an appearance time difference between two or more pulse waves whose order of appearance of the pulse wave pattern satisfies a predetermined condition can be used. For example, an appearance time difference between the second one and the second-to-last one of the order of appearance of the pulse wave pattern may be used. However, a more accurate calculation of the pulse wave propagation velocity can be expected by selecting a region such that the appearance time difference is as large as possible, for example, selecting the first and the last.

As will be described later, among all the rectangular regions, a pulse wave in a rectangular region in which a pulse wave satisfying a predetermined quality is detected and whose order of appearance of the pulse wave satisfies the above-described predetermined condition may be used. Thus, even if there is a region where a high-quality pulse wave cannot be detected, the blood pressure can be estimated using the pulse wave detected in other regions, and the availability of the device is improved.

The blood vessel structure of the face is different for each person, and it is difficult to specify the blood vessel structure of each person. However, in each person, it is estimated that the blood vessel structure does not change in a short period of time. In other words, it is estimated that the blood flow path from the region where the pulse wave pattern first appears to the region where the pulse wave pattern appears last is substantially constant for each person. Therefore, by estimating the distance of the path and using the estimated distance, the pulse wave propagation velocity can be calculated from the appearance time difference. The distance of this path may be estimated in advance based on data measured in advance using a biological measurement device. This may be a different value for each person, or a common value when individual differences do not matter (for example, when the accuracy required for the estimated value of blood pressure is not so high, or when it is only required to know changes in blood pressure over time for each person).

In addition, as illustrated in FIGS. 13 and 14, when a face of a person is further divided into a plurality of regions and a pulse wave is to be detected in each region, the pulse wave is not always detected in all regions due to noise. In general, there can be such a situation that a pulse wave can be detected at a certain time but a pulse wave cannot be detected at another time in the same region. However, it is estimated that, at any time, the distance of the blood flow path from the region where the pulse wave pattern first appears to the region where the pulse wave pattern appears last among the regions where the pulse wave is detected at that time is substantially constant for each person.

From this, the biological information detection device of the present embodiment extracts, from a plurality of regions, the region whose appearance order is the first (region (4) in the example in FIG. 13 and FIG. 14) and the region whose appearance order is the last (region (1) in the example in FIG. 13 and FIG. 14) where the pulse wave having a quality satisfying a predetermined condition is detected (which can be used for calculation of a propagation velocity, for example, can specify a time of a sufficiently reliable maximum value or minimum value), and calculates the pulse wave propagation velocity from the appearance time difference of the pulse wave pattern therebetween.

Figure 5:
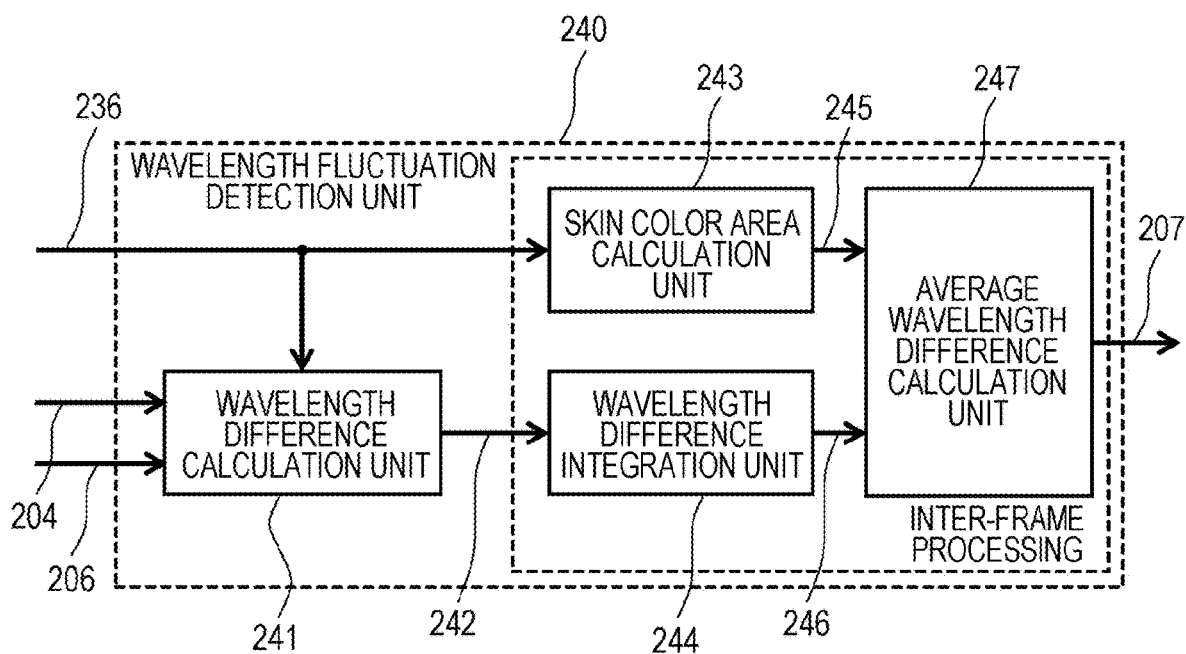
FIG. 5 is a block diagram illustrating an example of a wavelength fluctuation detection unit of the biological information detection device according to the first embodiment of the present invention.

FIG. 5 is a block diagram illustrating an example of the wavelength fluctuation detection unit 240 of the biological information detection device according to the first embodiment of the present invention.

The wavelength fluctuation detection unit 240 includes a wavelength difference calculation unit 241, a skin color area calculation unit 243, a wavelength difference integration unit 244, and an average wavelength difference calculation unit 247. The wavelength difference calculation unit 241 receives the level signal 236 indicating the skin region, the wavelength data signal 204, and a delayed wavelength data signal 206 as inputs. When a signal of a pixel in the skin color region is input (that is, 1 is input as the level signal 236), the wavelength difference calculation unit 241 outputs a wavelength difference data signal 242 calculated from the input wavelength data signal 204 and delayed wavelength data signal 206 (that is, the difference between the wavelength data signal 204 at each time and the wavelength data signal 204 at a time before each time). When a signal of a pixel outside the skin color region is input, the wavelength difference calculation unit 241 outputs 0 value. The skin color area calculation unit 243 receives the level signal 236 indicating the skin color region as an input, counts the number of pixels of the skin color region for each frame, and outputs a skin color area signal 245. The wavelength difference integration unit 244 receives the wavelength difference data signal 242 of the skin region pixel as an input, integrates the wavelength difference for each frame, and outputs an integrated wavelength difference data signal 246. The average wavelength difference calculation unit 247 receives the skin color area signal 245 and the integrated wavelength difference data signal 246 as inputs, and outputs a wavelength difference data signal 207 averaged in the frame by dividing the integrated wavelength difference data by the skin color area (that is, for all pixels in one frame).

Figure 7:
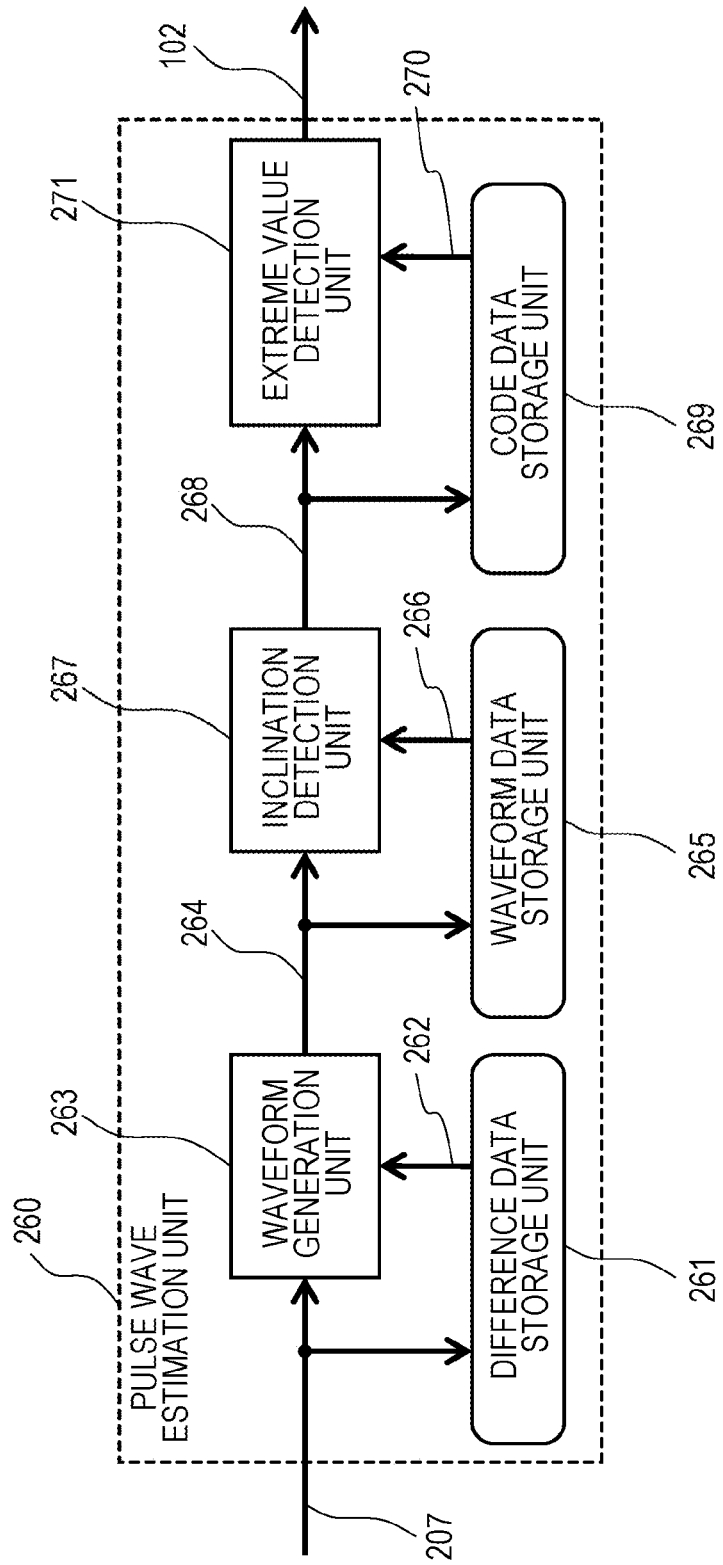
FIG. 7 is a block diagram illustrating an example of a pulse wave estimation unit of the biological information detection device according to the first embodiment of the present invention.

FIG. 7 is a block diagram illustrating an example of the pulse wave estimation unit 260 of the biological information detection device according to the first embodiment of the present invention.

The pulse wave estimation unit 260 includes a difference data storage unit 261, a waveform generation unit 263, a waveform data storage unit 265, an inclination detection unit 267, a code data storage unit 269, and an extreme value detection unit 271, and performs image processing for each frame. The difference data storage unit 261 receives the wavelength difference data signal 207 as an input and outputs a delayed wavelength difference data signal 262. The waveform generation unit 263 may be a smoothing filter that receives the wavelength difference data signal 207 and the delayed wavelength difference data signal 262 as inputs, and outputs a wavelength difference data signal 264 smoothed by wavelength data for a plurality of frames on a continuous time axis. The waveform data storage unit 265 receives the smoothed wavelength difference data signal 264 as an input, holds wavelength difference data for a plurality of frames, and outputs a smoothed delayed wavelength difference data signal 266. When pulse wave detection is performed by smoothing, if the detection region is small, the pulse wave signal may not be able to be determined due to noise.

Further, the waveform generation unit 263 may be a generation model such as a DNN (Deep Neural Network). That is, the waveform generation unit 263 may include a discriminator for estimating a pulse wave from wavelength fluctuation (wavelength difference data signal 207). In this case, as the learning data, pulse wave data measured in advance using a biological measurement device may be used. For example, as the learning data, data obtained by a pulse oximeter or a wristband type heart rate monitor may be used, or data obtained by integrating a waveform obtained from an electrocardiogram may be used. The learning may consist of a pair of a waveform at time t and a waveform at time t+1. The pulse wave can be estimated by repeating the prediction of the waveform at time t+2 from the waveform at time t+1 predicted using the learning data. As a result, an improvement in the accuracy of pulse wave estimation can be expected.

The inclination detection unit 267 compares the smoothed wavelength difference data signal 264 at a certain time with the signal output from the waveform data storage unit 265 (that is, the smoothed wavelength difference data signal 264 at an earlier time) to detect a change (that is, an inclination) in the smoothed wavelength difference data, and outputs a code data signal 268 for obtaining a code of the inclination. Specifically, the inclination detection unit 267 may compare the smoothed wavelength difference data signals of two consecutive frames, or may compare the wavelength difference data signals smoothed between the average frames of several consecutive neighboring frames. In the latter case, for example, the inclination detection unit 267 may compare the average of the wavelength difference data of a plurality of continuous frames with the average of the wavelength difference data of a plurality of previous consecutive frames to calculate the inclination of the difference. The code data storage unit 269 receives the code data signal 268 as an input, holds code data for a plurality of frames, and outputs a delayed code data signal 270.

The extreme value detection unit 271 receives the code data signal 268 and the delayed code data signal 270 as inputs, defines a frame whose code of the inclination changes from a positive value to a negative value (that is, change in the difference according to time turns from increasing to decreasing) as the maximum, and a frame whose code of the inclination changes from a negative value to a positive value (that is, change in the difference according to time turns from decreasing to increasing) as the minimum to obtain an extreme value, and outputs, for example, the maximum value (or the minimum value) as a pulse wave signal 102. Alternatively, the extreme value detection unit 271 may output information indicating the timing at which the maximal value (or the minimal value) is detected.

By smoothing the difference data signal by the waveform generation unit 263 as described above, erroneous detection of a pulse due to minute fluctuation of the difference data signal due to noise or the like is prevented. The inclination detection unit 267 detects a change (inclination) in the difference data between adjacent frames, and the extreme value detection unit 271 detects the maximum value or the minimum value of the difference data based on the result, thereby enabling generation of the pulse signal with accuracy. When the inclination detection unit 267 obtains the difference between the average frames of a plurality of consecutive neighboring frames, erroneous detection of a pulse is prevented as in the case of the above-described smoothing.

Figure 8:
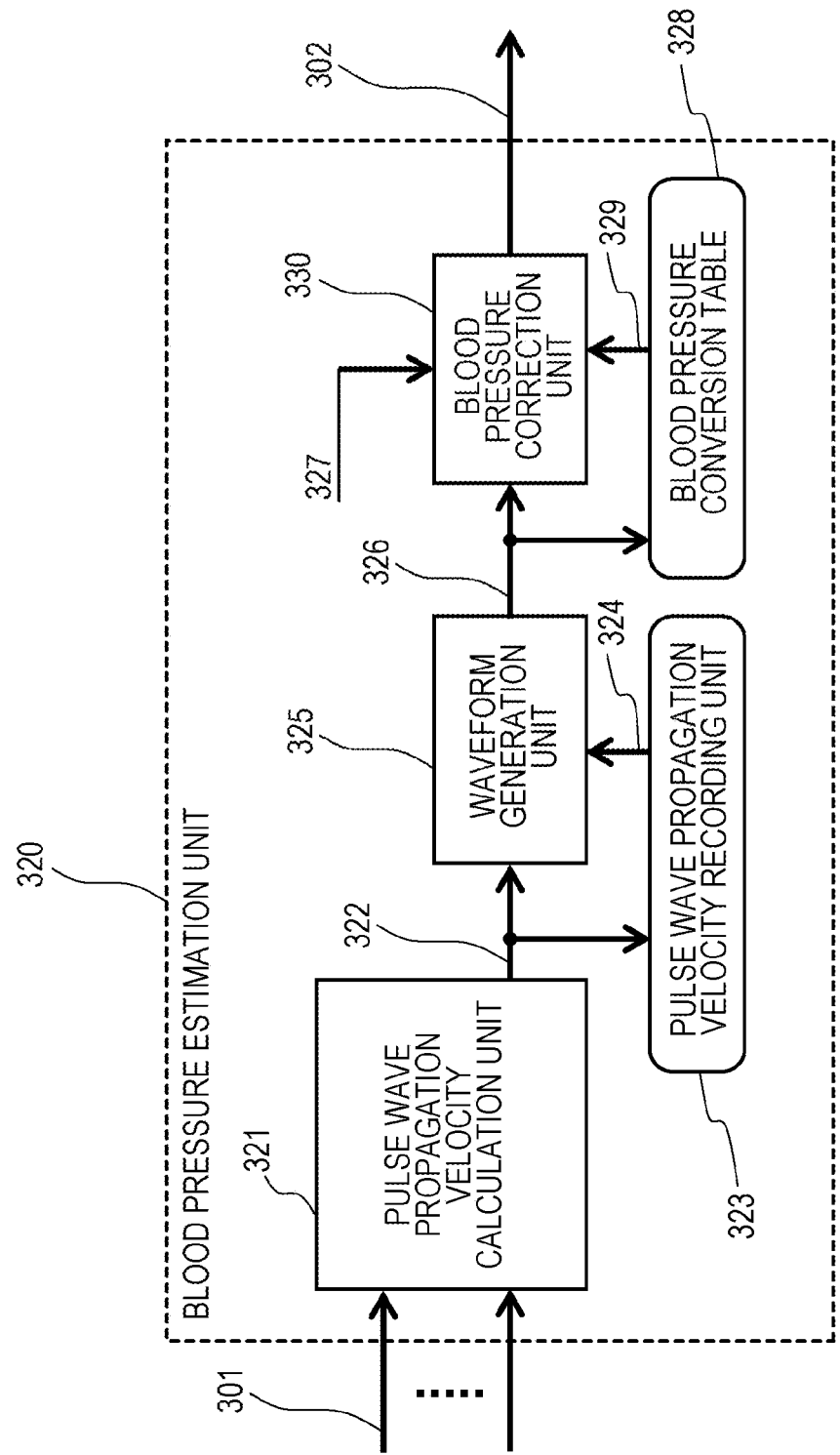
FIG. 8 is a block diagram illustrating an example of a blood pressure estimation unit of the biological information detection device according to the first embodiment of the present invention.

FIG. 8 is a block diagram illustrating an example of the blood pressure estimation unit 320 of the biological information detection device according to the first embodiment of the present invention.

The blood pressure estimation unit 320 includes a pulse wave propagation velocity calculation unit 321, a pulse wave propagation velocity storage unit 324, a waveform generation unit 325, a blood pressure conversion table 328, and a blood pressure correction unit 330.

The pulse wave propagation velocity calculation unit 321 receives the pulse wave signal 301 from each region as an input, and obtains a phase difference from the maximum and minimum pulse waves according to the appearance time of the pulse wave pattern, thereby calculating a pulse wave propagation velocity 322. The pulse wave propagation velocity storage unit 324 records the pulse wave propagation velocity over a plurality of frames. The waveform generation unit 325 calculates an average value of the pulse wave propagation velocities of a plurality of frames. The output of the waveform generation unit 325 corresponds to a blood pressure waveform. The blood pressure conversion table 328 receives a smoothed pulse wave propagation velocity signal 326 as an input, and outputs a blood pressure conversion signal 329 which is a source of a blood pressure value. The blood pressure correction unit 330 receives the smoothed pulse wave propagation velocity signal 326, the blood pressure conversion signal 329, and a blood pressure correction parameter 327 as inputs, corrects the blood pressure conversion signal, and outputs a blood pressure signal 302. The blood pressure correction parameter 327 is a parameter for correction based on age, gender, blood vessel radius, blood density, and the like.

In this configuration, the pulse wave propagation velocity calculation unit 321 has been described to include the blood pressure conversion table 328, but instead of the blood pressure conversion table 328, for example, a mathematical model such as the Moens-Korteweg equation may be used. If the ratio of the cross-sectional area of the inner diameter of the artery and the radius change and the wall thickness of the blood vessel wall are considered to be constant, when the blood pressure change is proportional to the incremental elastic modulus, and the ratio of the product of the radius and the blood density to the wall thickness of the blood vessel wall is constant, the incremental elastic modulus and the square of the pulse wave propagation velocity is proportional (Moens-Korteweg equation), so that the blood pressure change is represented by a proportional equation with the square of the pulse wave propagation velocity.

Further, the waveform generation unit 325 may be a generation model such as a DNN (Deep Neural Network). That is, the waveform generation unit 325 may include a discriminator for estimating the blood pressure waveform from the pulse wave propagation velocity. In this case, as the learning data, a blood pressure waveform measured in advance using a biological measurement device may be used. For example, the learning data may use a pulse wave propagation velocity or a waveform obtained by a tonometric blood pressure monitor or its square root. The learning may consist of a pair of a waveform at time t and a waveform at time t+1. The waveform can be generated by repeating the prediction of the waveform at time t+2 from the waveform at time t+1 predicted using the learning data. As a result, an improvement in the accuracy of blood pressure waveform generation can be expected.

As described above, the present embodiment focuses on the fact that the change amounts of the respective signal components of the RGB signals are different, and provides a detection method that is resistant to environmental changes by separating color components of the face image into the wavelength and the spectral intensity of the reflected light. Further, in the present embodiment, after the image region of the face or the exposed skin is divided, and the pulse wave signal is detected in each region, the pulse wave propagation velocity can be detected with accuracy based on the pulse wave signal and the phase difference statistically obtained in each region. With this, optical disturbance is excluded by detecting a pulse wave based on the wavelength fluctuation of the reflected light for each divided region, a phase difference is calculated from a pulse wave pattern of each region, and it is possible to provide a non-contact blood pressure measurement technique.

Here, in the configuration of the present embodiment, the camera 100 is a visible light color camera, and generates an image signal including three wavelength components of R, G, and B. However, this is only an example, and the camera 100 may have any configuration as long as the camera 100 is an imaging device that images reflected light from an object (for example, a human face) and outputs an image signal including components of a plurality of wavelengths. For example, at least one of the plurality of wavelengths may be included in an infrared or ultraviolet region. Further, a plurality of cameras 100 may be used to generate such an image signal.

In addition, the camera 100 may output an image signal including two wavelength components. For example, when only the R signal and the G signal are included in the image signal output by the camera 100, the generated color space is a region in which the hue ranges from R to G in the HSV color space illustrated in FIG. 10. However, if the skin color region 900 is included in the region, the same processing as described above can be performed.

Further, in the above example, the RGB signal is converted into a signal in the HSV color space. However, as long as the color space includes hue and brightness, the RGB signal may be converted into a signal in another color space such as an HSL (Hue Saturation Lightness) color space. In any case, a detection method that is resistant to environmental changes can be provided by detecting wavelength fluctuation based on hue signals. For example, in the case of the HSL color space, luminance is acquired as brightness, that is, intensity.

Further, as in the conventional method, the pulse wave may be calculated using individual signals such as green without performing the conversion in the color space as described above, or independent component analysis may be used instead of the color space as described above.

Second Embodiment

In the first embodiment, description is made of the biological information detection device that excludes optical disturbance by detecting a pulse wave based on the wavelength fluctuation of the reflected light for each divided region from the captured face image, calculates a phase difference from a pulse wave pattern of each region, and estimates the blood pressure. In a second embodiment, a configuration including adaptive processing based on the brightness of an image in the first embodiment according to the present invention will be described. Except for the differences described below, each part of the biological information detection device of the second embodiment has the same function as each part denoted by the same reference numeral in the first embodiment, and hence description thereof is omitted.

The configuration of the biological information detection device of the second embodiment is the same as the configuration of the biological information detection device of the first embodiment illustrated in FIG. 1 and the like, except for the reflected light analysis unit 220, the wavelength fluctuation detection unit 240, and the signal connecting these components.

Figure 3:
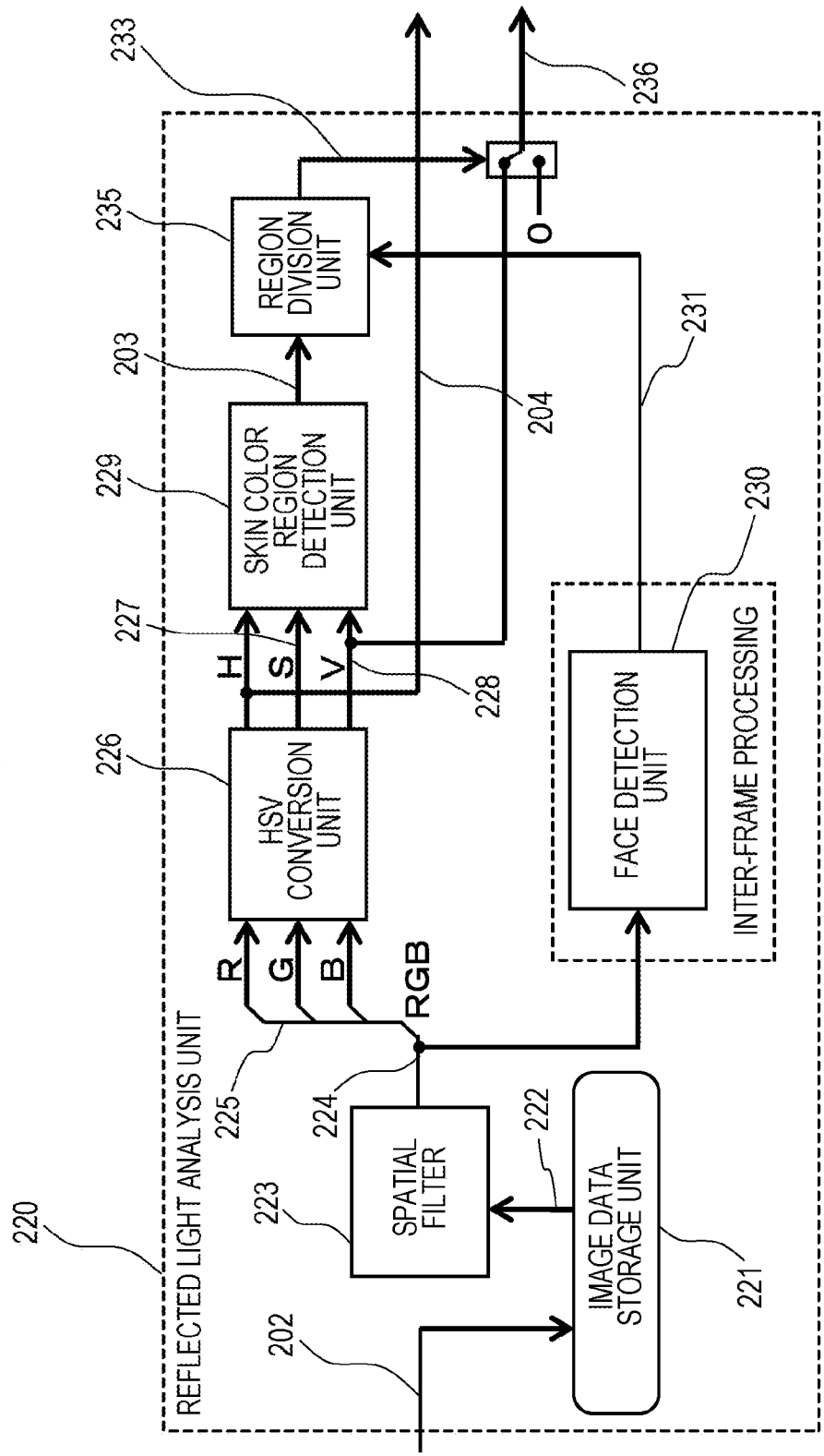
FIG. 3 is a block diagram illustrating an example of the reflected light analysis unit including a skin color region detection unit based on a color value level of the biological information detection device according to a second embodiment of the present invention.

FIG. 3 is a block diagram illustrating an example of the reflected light analysis unit 220 including the skin color region detection unit 229 based on the color value level of the biological information detection device according to the second embodiment of the present invention.

The reflected light analysis unit 220 includes an image data storage unit 221, a spatial filter 223, an HSV conversion unit 226, and a skin color region detection unit 229, and performs image processing for each pixel. The image data storage unit 221 receives the RGB signal 202 as an input and outputs a delayed RGB signal 222 having a line delay corresponding to a tap of a convolution kernel. The spatial filter 223 receives the delayed RGB signal 222 as an input, and weights and averages, for example, a pixel of interest and its surrounding pixels and outputs a smoothed RGB signal 224. The HSV conversion unit 226 receives the unpacked signal 225 obtained by decomposing the smoothed RGB signal 224 into R, G, and B signals as an input, and converts them into the H signal (hue), that is, the wavelength data signal 204, the S signal (saturation) 227, and the V signal (color value) 228.

The skin color region detection unit 229 receives the H signal (hue) 204, the S signal (saturation) 227, and the V signal (color value) 228 as inputs, and outputs the binary level signal 203 (mask signal) indicating the skin color region.

The reflected light analysis unit 220 in FIG. 3 further includes the face detection unit 230 and the region division unit 235. The face detection unit 230 receives the smoothed RGB signal 224 as an input, performs face detection by, for example, the Viola-Jones method, and outputs a face region signal 231. The region division unit 235 receives the face region signal 231 output from the face detection unit 230 and the level signal 203 output from the skin color region detection unit 229 as inputs, divides the face region into a plurality of regions, and outputs a binary level signal 233 indicating the skin color region.

The reflected light analysis unit 220 outputs the level signal 236 by switching the color value signal 228 according to the binary level signal 233. That is, the value of the level signal 236 of the second embodiment is 0 for pixels outside the skin color region, and the value of the color value of the pixel for the pixels inside the skin color region.

Figure 6:
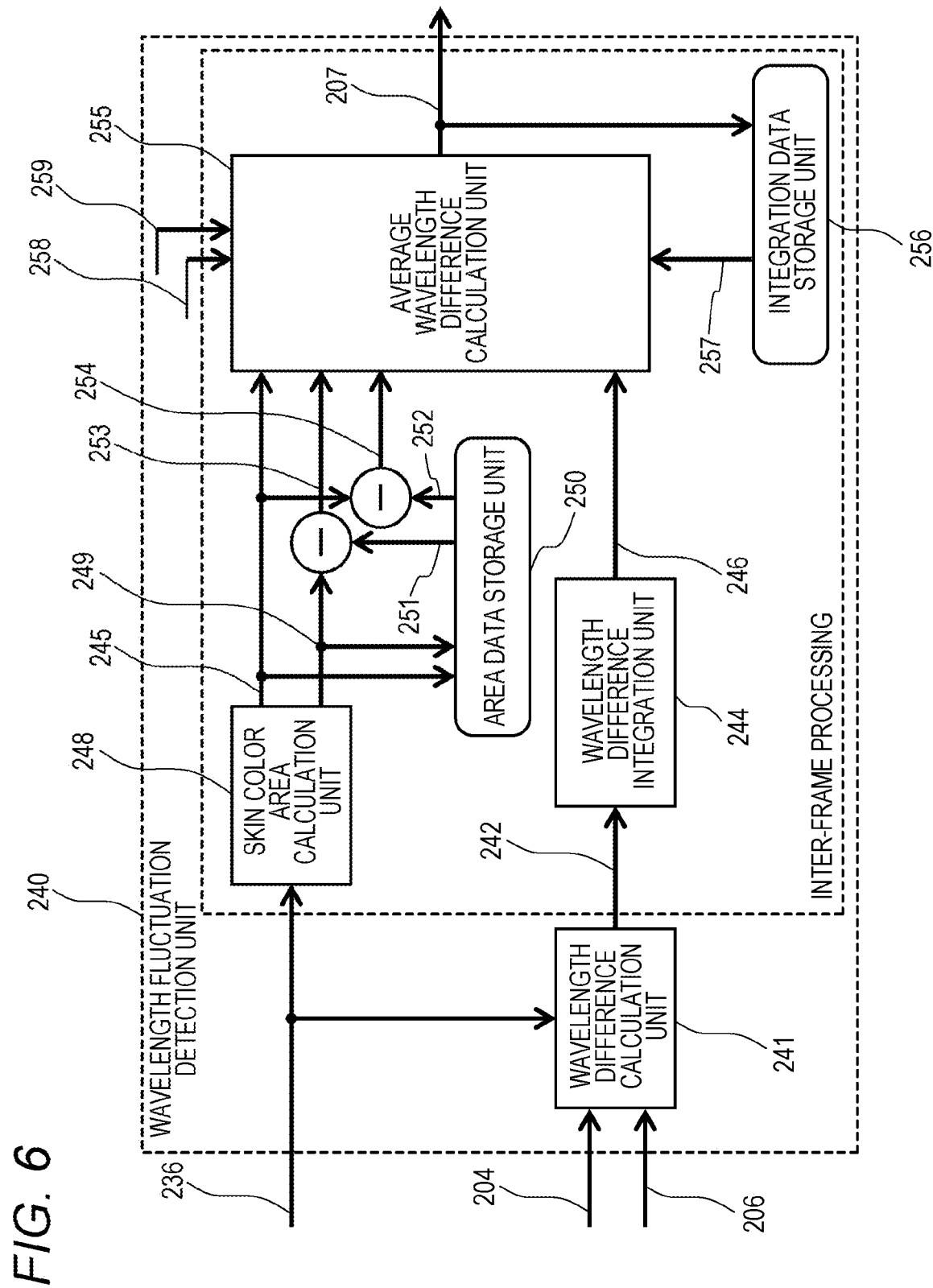
FIG. 6 is a block diagram illustrating an example of the wavelength fluctuation detection unit to which the color value level of the biological information detection device according to the second embodiment of the present invention is applied.

FIG. 6 is a block diagram illustrating an example of the wavelength fluctuation detection unit 240 to which the color value level of the biological information detection device according to the second embodiment of the present invention is applied.

The wavelength fluctuation detection unit 240 includes a wavelength difference calculation unit 241, a skin color area calculation unit 248, an area data storage unit 250, the wavelength difference integration unit 244, an integration data storage unit 256, and an average wavelength difference calculation unit 255.

The wavelength difference calculation unit 241 receives the level signal 236 indicating the skin color region, the wavelength data signal 204, and the delayed wavelength data signal 206 as inputs. When a signal of a pixel in the skin color region is input (that is, 1 is input as the level signal 236), the wavelength difference calculation unit 241 outputs the wavelength difference data signal 242 calculated from the input wavelength data signal 204 and delayed wavelength data signal 206. When a signal of a pixel outside the skin color region is input, the wavelength difference calculation unit 241 outputs 0 value.

The skin color area calculation unit 248 receives the signal 236 including the color value level indicating the skin color region as an input, counts the number of pixels outside the skin color region, that is, the number of pixels other than 0 value for each frame, and outputs the skin color area signal 245 indicating the area of the skin color region, and a color value level signal 249 indicating the brightness of the skin color region.

The area data storage unit 250 receives the skin color area signal 245 and the color value level signal 249 as inputs, and outputs a delayed skin color area signal 252 and a delayed color value level signal 251. The wavelength difference integration unit 244 receives the wavelength difference data signal 242 of the skin color region pixel as an input, integrates the wavelength difference for each frame, and outputs the integrated wavelength difference data signal 246.

The integration data storage unit 256 receives the wavelength difference data signal 207 as an input, holds data between a plurality of frames, and outputs a delayed integrated wavelength data signal 257. The average wavelength difference calculation unit 255 receives the skin color area signal 245, a color value level difference signal 253 between frames, a skin color area difference signal 254 between frames, the integrated wavelength difference data signal 246, and the delayed integrated wavelength data signal 257 as inputs, and outputs the wavelength difference data signal 207 averaged in the frame by dividing the integrated wavelength difference data by the skin color area.

The color value level difference signal 253 between frames is a difference between the color value level signal 249 of each frame and the color value level signal 249 of the previous (for example, immediately preceding) frame stored in the area data storage unit 250. The larger the value, the greater the change in the color value level. The skin color area difference signal 254 between frames is a difference between the skin color area signal 245 of each frame and the skin color area signal 245 of the previous (for example, immediately preceding) frame stored in the area data storage unit 250. The larger the value, the larger the change in the skin color area.

When a sudden change in external light occurs, that is, when a color value level difference signal 253 is larger than a color value level difference threshold value 258, the average wavelength difference calculation unit 255 may output, instead of the average wavelength difference data calculated from the integrated wavelength difference data signal 246 and the skin color area signal 245 of the current frame, the delayed integrated wavelength data signal 257 (for example, the output wavelength difference data signal 207 calculated from the integrated wavelength difference data signal 246 and the skin color area signal 245 of the past frame such as the previous frame) as the wavelength difference data signal 207 relating to the current frame, or may output the average value of the delayed integrated wavelength data signal 257 and the average wavelength difference data calculated from the integrated wavelength difference data signal 246 and the skin color area signal 245 of the current frame as the wavelength difference data signal 207 relating to the current frame. This suppresses erroneous detection due to a sudden change in external light.

Similarly, when change in the detected skin color region is large, that is, when the skin color area difference signal 254 is larger than a skin color area difference threshold value 259, the average wavelength difference calculation unit 255 may output, instead of the average wavelength difference data of the current frame, the delayed integrated wavelength data signal 257 or the average value of the delayed integrated wavelength data signal 257 and the average wavelength difference data calculated from the integrated wavelength difference data signal 246 and the skin color area signal 245 of the current frame as the wavelength difference data signal 207 relating to the current frame.

Examples of a system including the configuration described in the embodiments of the present invention include a PC including an imaging unit, an image output unit, and a storage unit, a mobile terminal, a TV, a car navigation device, and the like.

Figure 15A:
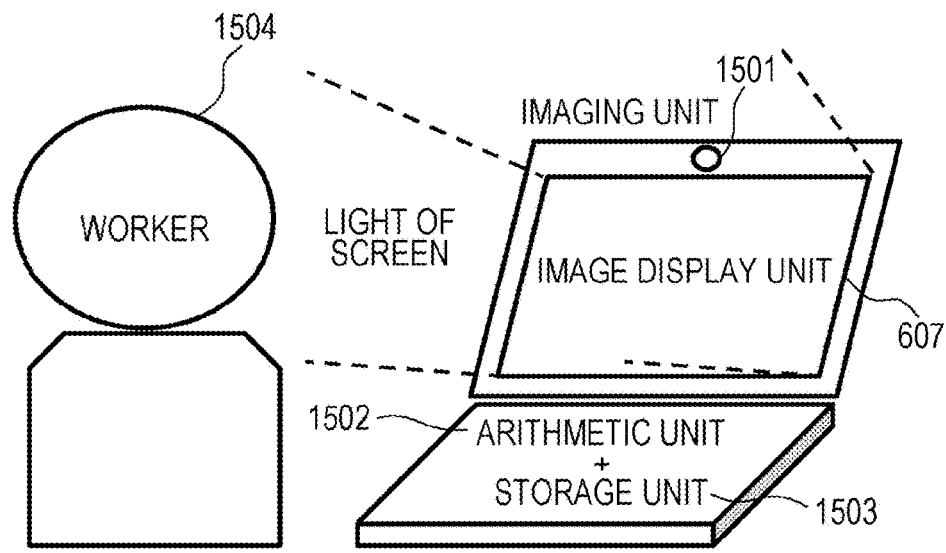
FIG. 15A is a diagram illustrating an example of a system including the biological information detection device according to the second embodiment of the present invention.

FIG. 15A is a diagram illustrating an example of a system including the biological information detection device according to the second embodiment of the present invention.

FIG. 15A illustrates, as an example, a PC (Personal Computer) including an imaging unit 1501, an image display unit 607, an arithmetic unit 1502, and a storage unit 1503. The imaging unit 1501 includes, for example, the camera 100. The image display unit 607 is, for example, a display device (for example, a liquid crystal display device) for displaying data and the like output from the data output unit 103. The arithmetic unit 1502 and the storage unit 1503 execute processing for realizing the function of the biological information detection device of the present embodiment. For example, the processing of the reflected light analysis unit 220, the local pulse wave detection unit 400, the blood pressure estimation unit 320, and the data output unit 103 may be realized by the arithmetic unit 1502 executing a program stored in the storage unit 1503.

The light of the screen output from the image display unit 607 hits the face of a worker 1504 (that is, the person whose biological information is to be detected by the biological information detection device), and the reflected light is imaged by the imaging unit 1501. For example, the arithmetic unit 1502 and the storage unit 1503 execute the processing of the second embodiment using the captured image, whereby biological information such as the blood pressure of the worker 1504 is measured.

As application examples of the biological information detection device of the present invention, there are given a system for estimating biological information such as a pulse and a blood pressure during VDT work using a PC for health management, a system for estimating a human state such as stress and emotion, a driver monitoring system for monitoring a driver's health condition before or during driving, a suspicious person monitoring system at an airport, and a system for monitoring sudden changes in the condition of elderly people or infants.

Figure 15B:
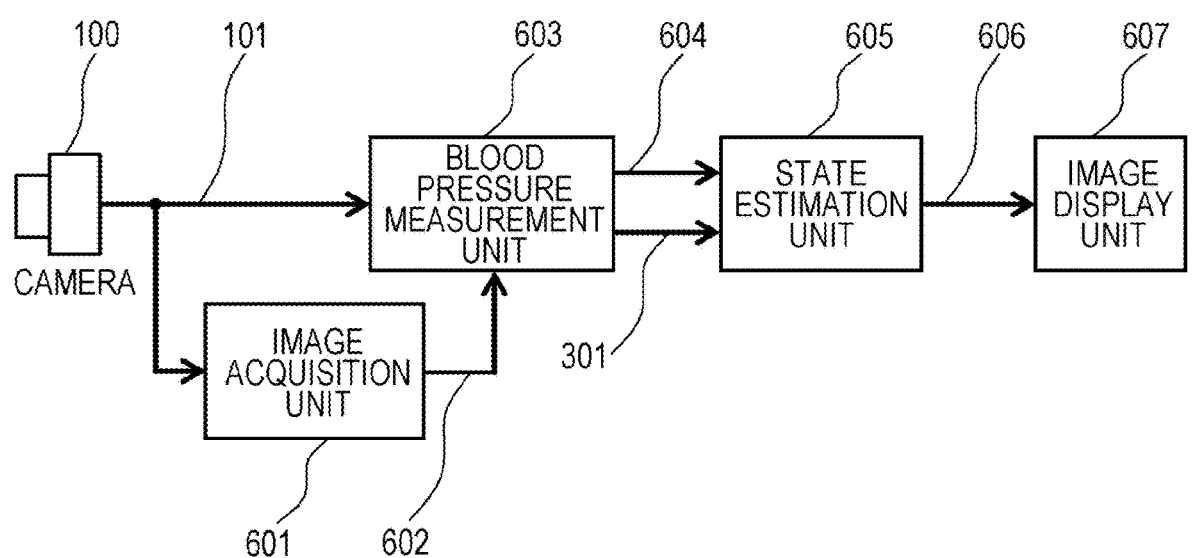
FIG. 15B is a block diagram illustrating an example of a configuration of a system including the biological information detection device according to the second embodiment of the present invention.

FIG. 15B is a block diagram illustrating an example of a configuration of the system including the biological information detection device according to the second embodiment of the present invention.

This configuration includes the built-in or externally connected camera 100, an image acquisition unit 601 that captures a screen image and outputs an average color luminance signal 602, a blood pressure measurement unit 603 that outputs a blood pressure signal 604 and the pulse wave signal 301, a state estimation unit 605 that estimates stress and emotion from a pulse and a blood pressure, and an image display unit 607 that displays state information 606. The image acquisition unit 601 corresponds to, for example, the image acquisition unit 201 in FIG. 1. Further, the blood pressure measurement unit 603 corresponds to, for example, the reflected light analysis unit 220, the local pulse wave detection unit 400, and the blood pressure estimation unit 320 in FIG. 1.

By subtracting the average color luminance signal 602 output from the image acquisition unit 601, the influence of disturbance due to light from the screen of the image display unit 607 can be eliminated.

Further, the state estimation unit 605 converts, for example, the elapsed time between the minimum values of the pulse wave signal into a frequency within a certain period, thereby calculating LF (Low Frequency: 0.04 to 0.15 Hz) and HF (High Frequency: 0.15 to 0.50 Hz), and can estimate stress, emotion, and the like based on any of LF, HF, and a blood pressure value, or any combination thereof. For example, the stress may be estimated by obtaining the stress index LF/HF, and the emotion may be estimated by using the HF, LF, and a blood pressure value.

Although this configuration has been described using a PC, the present invention can be similarly applied to mobile phones, TVs, and car navigation systems. In addition, this configuration can be divided into processing of the terminal and processing of the server. For example, the blood pressure measurement unit 603 and the state estimation unit 605 may be implemented on the server side, and on the terminal side, the image acquired by the image acquisition unit 601 may be transmitted to the server, and the state estimation result by the server may be received.

According to the above configuration, in the pulse wave detection, erroneous detection due to the influence of the sudden fluctuation of the external light and the sudden fluctuation of the photographed skin color area can be suppressed, and the measurement can be suitably performed.

Although the system including the biological information detection device according to the second embodiment of the present invention has been described with reference to FIGS. 15A and 15B, a similar system can be configured using the biological information detection device according to the first embodiment.

The present invention is not limited to the embodiments described above, but includes various modifications. For example, the embodiments described above have been described in detail for better understanding of the present invention, and the present invention is not necessarily limited to those having all the configurations described above. Further, a part of the configuration of one embodiment can be replaced with the configuration of another embodiment, and the configuration of one embodiment can be added to the configuration of another embodiment. In addition, it is possible to add, delete, and replace other configurations for a part of the configuration of each embodiment.

Each of the above-described configurations, functions, processing units, processing means, and the like may be realized by hardware by designing a part or all of them with, for example, an integrated circuit. Further, each of the above-described configurations, functions, and the like may be realized by software by interpreting and executing a program that realizes each function by the processor. Information such as programs, tables, and files that realize each function can be stored in a storage device such as non-volatile semiconductor memories, hard disk drives, or SSDs (Solid State Drives), or a computer readable non-transitory data storage medium such as IC cards, SD cards, or DVDs.

Further, only the control lines and information lines that are considered necessary are given, and all the control lines and information lines are not necessarily given for the product. Actually, it may be considered that almost all the components are connected to each other.

What is claimed is:

1. A blood pressure sensor to provide improved estimation of blood pressure, comprising:
   a camera that collects images; and
   a processor operatively coupled with and in communication with the camera, the processor configured to:
   acquire the images from the camera, the images composed of image signals including a plurality of wavelength components obtained by capturing reflected light from an object;
   divide the images into a plurality of regions for each frame;
   detect a pulse wave based on wavelength fluctuation between frames for each of the regions; and
   estimate a blood pressure by calculating propagation velocity of the pulse wave based on an appearance time difference of patterns of the pulse waves in two or more regions extracted based on an appearance order of the patterns of the pulse waves in the plurality of regions, wherein a pulse wave is estimated by repeating a prediction of a pulse wave at a first time from a pulse wave at an earlier time to the first time using learned information from a previous iteration to improve the estimation.

2. The blood pressure sensor according to claim 1, wherein the processor is configured to divide the images into a predetermined number of the regions for each of the frames, and
detect the pulse wave in a region where a skin color is detected among the predetermined number of the regions.

3. The blood pressure sensor according to claim 1, detect a face of a person included in the images,
divide a region of the images where a face is detected into a plurality of regions for each of the frames, and
detect the pulse wave in the divided plurality of regions.

4. The blood pressure sensor according to claim 1, wherein the processor includes a discriminator for estimating the pulse wave from the wavelength fluctuation, which is adjusted based on pulse wave data measured using a biological measurement device in advance.

5. The blood pressure sensor according to claim 1, wherein processor includes a discriminator for estimating a blood pressure waveform from the propagation velocity of the pulse wave, which is adjusted based on pulse wave data measured using a biological measurement device in advance, and
wherein the processor estimates the blood pressure based on a blood pressure waveform estimated by the discriminator.

6. The blood pressure sensor according to claim 1, wherein the appearance order of the patterns of the pulse waves is an appearance order of maximum values or minimum values of the pulse waves, and the appearance time difference of the patterns of the pulse waves is an appearance time difference of the maximum values or the minimum values of the pulse waves.

7. The blood pressure sensor according to claim 1, wherein the processor extracts, from the plurality of regions, a region whose appearance order of the patterns of the pulse waves is the first and a region whose appearance order of the patterns of the pulse waves is the last, and calculates the propagation velocity of the pulse wave based on the appearance time difference of the patterns of the pulse waves in the extracted regions.

8. The blood pressure sensor according to claim 7, wherein the processor holds a conversion table for converting the propagation velocity of the pulse wave into a blood pressure, and
wherein the processor estimates the blood pressure based on the propagation velocity of the pulse wave and the conversion table.

9. The blood pressure sensor according to claim 7, wherein the processor estimates the blood pressure by applying a predetermined mathematical model to the propagation velocity of the pulse wave.

10. The blood pressure sensor according to claim 7, wherein the processor extracts, from the plurality of regions, a region whose appearance order of the patterns of the pulse waves is the first and a region whose appearance order of the patterns of the pulse waves is the last where a pulse wave having a quality satisfying a predetermined condition is detected.

11. A blood pressure sensing method, which is executed by a blood pressure sensor to provide improved estimation of blood pressure, the method comprising:

a procedure in which the blood pressure sensor acquires images composed of image signals including a plurality of wavelength components obtained by capturing reflected light from an object;

a procedure in which the blood pressure sensor divides the images into a plurality of regions for each frame;

a procedure in which the blood pressure sensor detects a pulse wave based on wavelength fluctuation between frames for each of the regions; and a procedure in which the blood pressure sensor estimates a blood pressure by calculating propagation velocity of the pulse wave based on an appearance time difference of patterns of the pulse waves in two or more regions extracted based on an appearance order of the patterns of the pulse waves in the plurality of regions, wherein a pulse wave is estimated by repeating a prediction of a pulse wave at a first time from a pulse wave at an earlier time to the first time using learned information from a previous iteration to improve the estimation.

* * * * *